(12) United States Patent
Bassez et al.

(10) Patent No.: US 9,999,548 B2
(45) Date of Patent: Jun. 19, 2018

(54) METHOD FOR DETERMINING A SIZE GRID

(71) Applicant: LABORATOIRES INNOTHERA, Arcueil (FR)

(72) Inventors: Sophie Bassez, Villebon sue Yvette (FR); François Cros, Ivry sur Seine (FR)

(73) Assignee: LABORATOIRES INNOTHERA

( * ) Notice: Subject to any disclaimer, the term of this patent is extended or adjusted under 35 U.S.C. 154(b) by 114 days.

(21) Appl. No.: 15/243,164

(22) Filed: Aug. 22, 2016

(65) Prior Publication Data

US 2017/0049632 A1    Feb. 23, 2017

(30) Foreign Application Priority Data

Aug. 20, 2015   (FR) ...................................... 15 57843

(51) Int. Cl.
  *A41H 1/02*   (2006.01)
  *A61F 13/08*  (2006.01)
  *G06F 19/00*  (2018.01)

(52) U.S. Cl.
  CPC .............. *A61F 13/08* (2013.01); *G06F 19/30* (2013.01)

(58) Field of Classification Search
  CPC ....................................................... A41H 1/02
  USPC ........................................ 33/2 A, 6, 11, 512
  See application file for complete search history.

(56) References Cited

U.S. PATENT DOCUMENTS

| | | | | |
|---|---|---|---|---|
| 2,537,417 A | * | 1/1951 | Merske | ................... B65D 85/18 |
| | | | | 206/281 |
| 7,650,702 B2 | * | 1/2010 | Jensen | ...................... A41H 1/10 |
| | | | | 2/400 |
| 2012/0035510 A1 | * | 2/2012 | Cros | ....................... A61F 13/08 |
| | | | | 600/592 |
| 2013/0131572 A1 | * | 5/2013 | Cros | ......................... A61F 5/40 |
| | | | | 602/75 |
| 2014/0136560 A1 | | 5/2014 | Golshani | |

(Continued)

FOREIGN PATENT DOCUMENTS

EP    1 727 060 A1    11/2006

OTHER PUBLICATIONS

Apr. 7, 2016 Search Report issued in French Application No. 1557843.

(Continued)

*Primary Examiner* — G. Bradley Bennett
(74) *Attorney, Agent, or Firm* — Oliff PLC

(57) ABSTRACT

A method for determining a size grid, the method comprising following steps: a) determination of N morphological parameters, N being ≥2; b) acquisition of a set of values of the parameters for a sample of a targeted population of individuals, each individual being associated with an individual point supplying, for each parameter, a value of the parameter; c) independently of steps a) and b), determination of rate of coverage of sample to be covered by the grid; d) determination of a set of coverage zones, each coverage zone being a set of individual points relating to a set of individuals for which a same orthesis according to the model is adapted and thus corresponding to a size adapted to set of individuals; the number of coverage zones being determined such that percentage of individual points included in at least one coverage zone is ≥ the desired coverage rate.

12 Claims, 1 Drawing Sheet

(56) References Cited

U.S. PATENT DOCUMENTS

2014/0298667 A1* 10/2014 Alkhalaf .............. A61B 5/1077
                                                    33/514.2
2014/0379515 A1   12/2014 Hornbuckle
2016/0338644 A1* 11/2016 Connor ................ A61B 5/6804
2017/0319395 A1* 11/2017 Cros ....................... A61F 13/08
2017/0333256 A1* 11/2017 Bassez ................... A61F 13/08
2018/0010902 A1*  1/2018 Gong ....................... G01B 7/16

OTHER PUBLICATIONS

Creasy, Robert, "Performance, Physiological, and Perceptual Effects of Wearing Graduated Compressor Stockings During Running," (2008), XP055263531.

* cited by examiner

METHOD FOR DETERMINING A SIZE GRID

TECHNICAL FIELD

The present invention relates to a method for determining a size grid for an elastic vein compression (CVE) orthesis model, indicated in cases of vein inadequacy of a lower limb of a patient.

The invention relates also to a grid and the sizes determined by means of such a method, and the templates corresponding to these sizes.

STATE OF THE ART

The elastic vein compression ortheses, formerly known as "compression stockings" (or hose) or "compression tights", are textile medical devices producing a therapeutic effect through compression of the lower limbs, unlike the "support stockings" (or even "support hose" or "anti-fatigue stockings") and the "fashion stockings", which are not medical devices with therapeutic aim.

The elastic vein compression ortheses are designed to produce a therapeutic effect through compression of the lower limb over a greater or lesser extent, usually with an upwardly decreasing compression profile from the ankle.

Since the morphology of the lower limbs is different from one patient to another, an orthesis model is conventionally declined into a number of sizes in order to satisfy the market targeted. A size of a model is conventionally characterized by particular dimensions for the ortheses having said size. The elasticity of the orthesis does however allow one size to suit patients having lower limbs of different dimensions.

The set of the sizes of a model is called "size grid".

To limit the costs, the manufacturers of ortheses need to reduce the number of size grids.

One aim of the invention is to meet this need, at least partially.

SUMMARY OF THE INVENTION

The invention proposes a method for determining a size grid for an elastic vein compression orthesis model, said method comprising the following steps:
a) determination of N morphological parameters, N being greater than or equal to 2;
b) acquisition of a set of values of said parameters of a targeted population of individuals, each individual of the sample being associated with an individual point supplying, for each parameter, a value of said parameter;
c) independently of the steps a) and b), determination of a rate of coverage of said sample to be covered by said grid, or "desired coverage rate";
d) determination of a set of coverage zones, each coverage zone being a set of individual points relating to a set of individuals for which a same orthesis according to said model is adapted (that is to say may provide a treatment solution) and thus corresponding to a size adapted to said set of individuals;
the number of coverage zones being determined such that the percentage of individual points included in at least one coverage zone is greater than or equal to the desired coverage,
the set of the sizes corresponding to said coverage zones defining said size grid.

A method for determining size grid according to the invention may also comprise one or more of the following optional features:

in the step a), the number of morphological parameters is preferably 2 or 3;
in the step a), the parameters are preferably chosen from the group consisting of an ankle dimension, preferably an ankle perimeter, a calf dimension, preferably a calf perimeter, and a thigh dimension, preferably a thigh perimeter;
in the step b), the number of individual points is preferably greater than 500, preferably greater than 1000, preferably greater than 2000, preferably greater than 3000, preferably greater than 5000;
in the step b), the targeted population is a part of the population more likely to be affected by the treatment by the orthesis model than the rest of the population, or even is a part of the population having been treated by means of the orthesis model;
in the step c), the desired coverage rate is preferably greater than 90%, preferably greater than 95%, preferably 100%;
in the step d), the number of coverage zones is minimized;
the step d) comprises the following steps:
d1) for a first of said parameters $p_1$, subdivision into "first fractions" of a "first segment" representing all the values of the first parameter between the minimum and maximum bounds of the first parameter, said minimum and maximum bounds being determined such that said first segment covers more than 80%, preferably more than 90%, preferably more than 95%, even 100% of the number of individuals of the sample;
d2) successively, for each $n^{th}$ parameter $p_n$, from the second parameter to the last parameter $p_N$, for each $(n-1)^{th}$ fraction, subdivision into $n^{th}$ fractions of an $n^{th}$ segment representing all the values of the $n^{th}$ parameter lying between the minimum and maximum bounds of the $n^{th}$ parameter, said minimum and maximum bounds being determined such that said $n^{th}$ segment covers more than 80%, preferably more than 90%, preferably more than 95%, even 100% of the number of individuals of the $(n-1)^{th}$ fraction considered;
said segments being determined so as to define, after the processing of the last parameter, a set of coverage zones together covering a percentage of the population of the sample greater than or equal to the desired coverage rate,
each coverage zone consisting of a set of points each defined by N coordinates, all the $i^{th}$ coordinates of the points of a same coverage zone belonging to a same $i^{th}$ fraction;
preferably, there is at least one parameter $p_n$ for which all the $n^{th}$ fractions have the same width;
preferably, regardless of the parameter $p_n$, all the $n^{th}$ fractions have the same width;
the width of an $n^{th}$ fraction is less than or equal and, preferably greater than 0.8, to 0.9 times, preferably equal to the maximum variation amplitude of the values of the $n^{th}$ parameter that may be obtained by deformation of orthesis according to said model.

The invention relates also to an orthesis having a size from a size grid determined according to a method according to the invention.

The invention relates to an orthesis having, at rest, dimensions within the following ranges $P_i$, in cm:

| Ranges | | P0 | P1 | P2 | P3 | P4 | P5 | P6 | P7 |
|---|---|---|---|---|---|---|---|---|---|
| Ankle perimeter at rest | min | 14 | 15 | 15 | 17 | 17 | 18.5 | 18.5 | 20 |
| | max | 15 | 16 | 16 | 18 | 18 | 19.5 | 19.5 | 21 |
| Thigh perimeter at rest | min | 27.5 | 28 | 31.5 | 29.5 | 33 | 33 | 35.5 | 35 |
| | max | 28.5 | 29 | 32.5 | 30.5 | 34 | 34 | 36.5 | 36 | or within the following ranges $P_i'$, in cm:

| Ranges | | P0' | P1' | P2' | P3' | P4' | P5' | P6' | P7' |
|---|---|---|---|---|---|---|---|---|---|
| Calf perimeter at rest | min | 20 | 19 | 20.5 | 21.5 | 22.5 | 24 | 24.5 | 25.5 |
| | max | 21 | 20 | 21.5 | 22.5 | 23.5 | 25 | 25.5 | 26.5 |
| Ankle perimeter at rest | min | 13.5 | 15 | 15 | 16.5 | 16.5 | 17.5 | 18.5 | 20 |
| | max | 14.5 | 16 | 16 | 17.5 | 17.5 | 18.5 | 19.5 | 21 |

In these tables, "min" and "max" define the lower and upper bounds of possible variation for the parameter concerned, respectively.

For example, the invention relates to an orthesis belonging to the range P0, that is to say having, at rest, an ankle perimeter of between 14 and 15 cm and a thigh perimeter of between 27.5 and 28.5 cm.

The invention also relates to an orthesis model for which the size grid is determined according to a method according to the invention.

The invention relates in particular to a set of ortheses of different sizes, according to a same model, each of said ortheses having, at rest, dimensions within one of the ranges $P_i$, or each of said ortheses having, at rest, dimensions within one of the above ranges $P_i'$.

In a preferred embodiment, said set comprises, for each size, at least one orthesis according to the model.

The invention relates also to a size grid comprising one or more, preferably only sizes of ortheses according to the invention. The implementation of a method according to the invention in particular makes it possible to obtain such a grid.

The invention relates also to a template of a lower limb of an animal body, in particular human, for example a wooden template, the dimensions of which correspond to a size according to the invention or, more generally, a size from a size grid determined by means of a method according to the invention.

The invention relates also to a set of templates according to the invention comprising one or more templates according to the invention, preferably comprising one template for each of the sizes of a grid according to the invention.

The invention relates also to a kit comprising:
a database containing, for at least two morphological parameters, parameter values for a sample of individuals representative of a targeted population, and
a template corresponding to values for said parameters resulting from a statistical analysis of the database, preferably corresponding to a size grid determined according to a method according to the invention.

The morphological parameters are preferably chosen from the parameters described previously in the context of the description of the method according to the invention.

BRIEF DESCRIPTION OF THE FIGURES

Other features and advantages will become more apparent on reading the following detailed description, and on studying the attached drawing in which.

DEFINITIONS

Figures 1, 2:
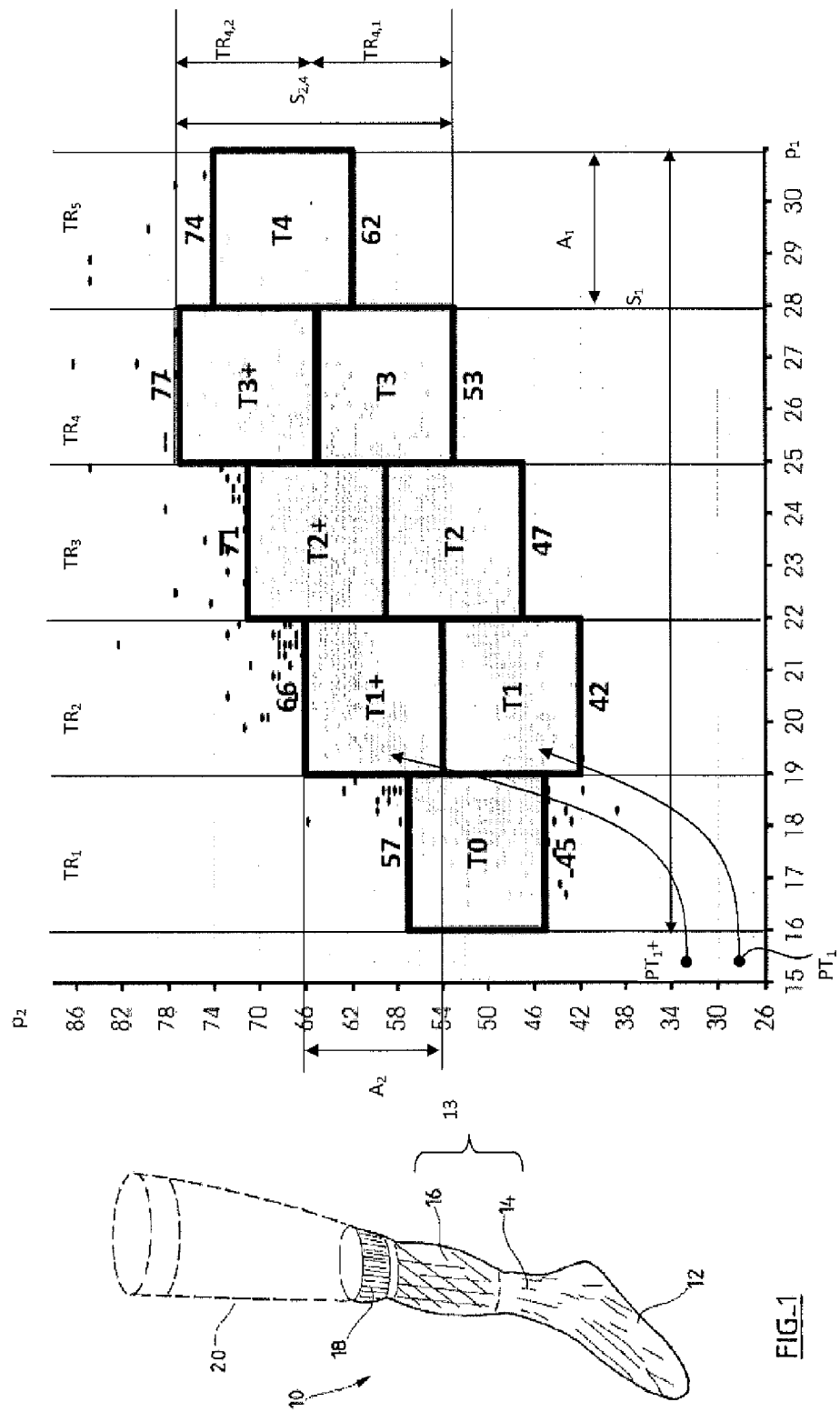
FIG. 1 schematically represents an orthesis according to the invention.
FIG. 2 represents points corresponding to a sample representative of a targeted population, and rectangular coverage zones, determined by following a method according to the invention.

A "size grid" is a set of sizes determined to cover a targeted population.

A "size" is conventionally a set of parameters relating to an orthesis which makes it possible to determine whether this orthesis is suited to an individual.

A size may in particular be conventionally defined by all the ranges, for the morphological parameters, which define a coverage zone in which the individual point corresponding to said individual belongs.

For example, if an orthesis is effective for the individuals of the targeted population whose ankle perimeter lies between 19 and 22 cm, and the thigh perimeter lies between 42 and 54 cm, the size may be defined by the following set ([19-22 cm]; [42-54 cm]). This size corresponds to the coverage zone T1 represented in FIG. 2.

Equivalently, a size may be defined by dimensions of the orthesis measured at rest. These dimensions correspond preferably to the morphological parameters which define the corresponding coverage zone. For example, for the coverage zone T1 represented in FIG. 2, the size may be (17 cm, 38 cm) and correspond to the ankle and thigh parameters in the horizontal position (twice the width lying flat) of the orthesis at rest measured at the corresponding level at the altitude of the ankle and of the thigh, respectively. Such sizes may be each represented by a "size point". In FIG. 2, $PT_1$ and $PT_1+$ designate the size points for the coverage zones T1 and T1+, respectively.

The "targeted" population consists of the individuals for whom the model aims to provide a treatment solution. The individuals for whom the model effectively provides a solution, that is to say for whom there is at least one orthesis according to the model capable of providing a treatment solution are said to be "covered". The different sizes of a model make it possible to "cover" a proportion of the targeted population greater than the targeted coverage rate.

A "morphological parameter" is a parameter of the body, and in particular of a lower limb of the body, relevant for determining a size. The perimeters, or "circumferences", of the ankle, calf and thigh are examples of morphological parameters. In one embodiment, the perimeters of the ankle, calf and thigh are measured at the levels where the ankle is thinnest and where the calf and the thigh are widest, respectively.

A "point" is a set of values of the morphological parameters corresponding to an individual ("individual point") or, when the size is defined by dimensions of the orthesis measured at rest, to a size ("size point"). Thus, an individual or size "point" provides, for an individual or size, respectively, the set of values of the corresponding morphological parameters.

For example, if the morphological parameters are the perimeter of the ankle and the thigh perimeter, the individual point (20 cm; 50 cm) corresponds to an individual for whom the perimeter of the ankle and the thigh perimeter are respectively 20 cm and 50 cm. This individual point belongs to the coverage zone T1 represented in FIG. 2. The corresponding size point is $PT_1$ (17 cm, 38 cm) and corresponds to ankle and thigh perimeters in the horizontal position (twice the width lying flat) of the orthesis at rest measured at the level corresponding to the altitude of the ankle and of the thigh, respectively.

A "coverage zone", associated with a size, combines all the individual points that an orthesis according to said size may reach, by deformation, by continuing to provide a satisfactory treatment solution to the corresponding individuals. In other words, a coverage zone for an orthesis is a set of points each providing a set of values of the parameters likely to be exhibited, in a service position, by this orthesis. If an individual is represented by an individual point of the coverage zone, the orthesis according to said size will therefore be able to provide him or her with a treatment solution. Unless indicated otherwise, "deformation" of an orthesis should be understood to mean a deformation maintaining a therapeutic effectiveness.

The coordinates of a size point correspond to dimensions of the orthesis "at rest", that is to say measured when the orthesis is not worn. Consequently, the size point does not normally belong to the corresponding coverage zone. It is in fact normally essential for the orthesis to be always deformed to exert a minimal pressure on the lower limb of any individual covered by the coverage zone. Obviously, the extent of a coverage zone depends on the "deformation capacities" of the orthesis, that is to say on the possibilities, for the orthesis, of being deformed while retaining its therapeutic action.

An orthesis "model", or "range", comprises the ortheses of a particular type, for example intended for a particular treatment.

The "altitude" corresponds to a level in the vertical direction when the orthesis is worn by a patient standing straight and upright. The adjectives "higher" and "lower" relate to the same reference frame.

The "service position" of an orthesis corresponds to a position of use, that is to say in which it is fitted over a lower limb of a patient and provides a satisfactory treatment.

On the contrary, the "at rest" position of an orthesis corresponds to a position lying flat, during which the orthesis is not worn, for example before first use thereof.

Unless otherwise indicated, "comprising", "containing", "having", "including" or their variations correspond to a non-exclusive inclusion.

DETAILED DESCRIPTION

In FIG. 1, the reference 10 generally designates an orthesis 10 according to the invention.

The orthesis 10, of generally tubular form, comprises a foot part 12 enveloping the foot and a leg part 13 comprising an ankle part 14 enveloping the ankle and a calf part 16 enveloping the calf.

The orthesis 10 extends to a level situated below the knee, in the case where the orthesis is "half-hose" (or "knee sock"). In the latter case, the orthesis is terminated by a terminal knitted part of the ribbed type called "ribbed terminal portion" 18.

The configuration in sock form is not limiting, and the orthesis 10 may also be produced in the form of a "thigh stocking", prolonged by a compressive thigh part 20. The orthesis 10 may also be produced in the form of tights, and/or without any foot part 12 (stocking or tights of "open foot" type).

Various adjoining parts of the orthesis 10 are preferably knitted continuously on a circular machine, according to conventional methods.

The effectiveness of an orthesis is closely linked to the matching of its dimensions to those of the lower limb to be treated. This is why a number of sizes are proposed for each orthesis model. The size grid must however be reduced, each addition of a size substantially increasing the production cost of the ortheses.

To determine a minimal grid, the method according to the invention comprises the steps a) to d). The detailed description which follows, in a nonlimiting manner, is illustrated by FIG. 2.

In the step a), at least two morphological parameters are determined that make it possible to assess whether an orthesis is suited to an individual. The values of the morphological parameters make it possible to distinguish the different sizes.

The number of parameters taken into account is not limited. The addition of parameters makes it advantageously possible to create sizes accurately corresponding to a part of the population, but also leads to a multiplication of the number of sizes of the grid. Preferably, the number of parameters is two or three, even four.

Hereinafter in the detailed description, the first and second morphological parameters $p_1$ and $p_2$ retained are the perimeter of the ankle and the perimeter of the thigh at predefined altitudes of the lower limb, for example defined by the Hohenstein morphological reference frame.

In the step b), independently of the step a), said morphological parameters are measured on a sample of individuals representative of the targeted population, that is to say for whom the orthesis model is intended, so as to construct a database. The database provides, for each individual of the sample, the values of said morphological parameters, that is to say, in the example chosen, the ankle perimeter and the thigh perimeter. Each pair of a value of an ankle perimeter and of a value of a thigh perimeter for a particular individual constitutes an individual "point". The French Institute of Textiles and Clothing (L'Institut Français du Textile et de l'Habillement (IFTH)) may in particular provide such a database.

FIG. 2 represents the points of a sample representative of the targeted population. The abscissa X axis represents the ankle perimeter, in cm. The ordinate Y axis represents the thigh perimeter, in cm.

The sample may be representative of the population of a country or a region and/or, preferably, representative of the population affected by the treatment for which the orthesis model is designed. For example, the targeted population may consist of French individuals, of female sex and over 45 years old.

In the step c), a percentage of the sample to be covered by said grid, or "desired coverage rate", is determined.

The desired coverage rate determines the percentage of the individuals of the sample for which at least one size of the model will be able to be appropriate. This percentage is therefore the ratio, expressed as percent, of the number of the individual of the sample having a morphology that at least a size of the model will have to fit, divided by the number of individuals in the sample. On FIG. 2, the coverage rate is the ratio of the number of points which are within at least one square ("block") divided by the number of represented points. Since the sample is representative of the targeted population, the desired coverage rate also determines the percentage of the individuals of the targeted population for which at least one size of the model will be able to be appropriate.

The desired coverage rate is preferably greater than 90%, more preferably greater than 95%, preferably 100%.

In the step d), the database is analyzed to determine the coverage zones and, consequently, a size grid.

The analysis of the database makes it possible in particular to determine the possible maximum and minimum bounds for the first parameter.

The "first segment" $S_1$ is a range of values for the first parameter delimited by lower and upper bounds determined for more than 80%, preferably more than 90%, preferably more than 95%, even 100% of the number of individuals of the sample to exhibit a value, for said first parameter, which belongs to said range.

For example, as represented in FIG. 2, the first segment $S_1$ can be [16.0 cm 31 cm] for the ankle perimeter, on the abscissa X axis.

Then, fractions of the first segment, called "first fractions" $TR_i$ are determined. The width of each first fraction must be less than or equal to the maximum variation amplitude of the first parameter $A_1$.

For example, since the first parameter is the ankle perimeter, if the maximum variation amplitude of the ankle perimeter for an orthesis is 3 cm, as represented in FIG. 2, each first fraction must exhibit a width less than or equal to 3 cm. Preferably, the width of the first fractions is equal to the maximum variation amplitude $A_1$ of the first parameter.

The width of the variation range or "maximum variation amplitude" depends on the deformation capacities, for the parameter concerned, of the orthesis according to the model of the orthesis.

An orthesis has in particular a variable geometry, such that a same orthesis can be used for several individuals exhibiting values for the morphological parameters which are similar. For example, the elasticity at the altitude of the calf makes it possible for a same orthesis to suit individuals for whom the calf perimeter varies within a variation range.

The maximum variation amplitude for the ankle perimeter preferably lies between 2 and 4 cm. The maximum variation amplitude for the thigh perimeter preferably lies between 8 and 14 cm. In FIG. 2, the maximum variation amplitudes A1 and A2 for the ankle and thigh perimeters are, respectively, 3 cm and 12 cm.

The maximum variation amplitude for a parameter can be defined such that, whatever the orthesis according to the model, the possible variation amplitude for the parameter concerned is always greater than or equal to said "maximum variation amplitude".

Preferably, the number of first fractions is minimized. To this end, preferably, the first fractions do not overlap one another. Preferably however, to avoid having no size suit a part of the targeted population, for example because individuals would not be represented in the sample, all the first fractions are contiguous, that is to say have bounds in common with the adjacent first fractions. Thus, in FIG. 2, apart from the first fractions $TR_1$ and $TR_5$ at the ends of the first segment, the upper and lower bounds of a first fraction correspond to lower and upper bounds, respectively, of adjacent fractions.

The number of first fractions $N_1$ is advantageously minimized. In the example of FIG. 2, $N_1$ is equal to 5.

The distribution of the individual points in each first fraction $TR_i$ (i=1 ... $N_1$) is variable according to the first fraction considered.

For each first fraction $TR_i$, a "second segment" $S_{2,i}$ is determined.

Each second segment $S_{2,i}$ (i=1 ... $N_1$) is then subdivided into $N_{i,2}$ second fractions $TR_{i,j}$ (j=1 ... $N_{i,2}$). The number and the width of the second fractions $TR_{i,j}$ dividing up a second segment $S_{2,i}$ may be identical or different from those of second fractions $TR_{i',k}$ dividing up another segment $TR_p$.

In the example of FIG. 2, the second segment $S_{2,4}$ of the first fraction $TR_4$, is for example [53 cm 77 cm] for the second parameter (thigh perimeter), represented on the coordinate Y axis.

The subdivision into second fractions of the first fraction $TR_4$ therefore leads to dividing up this first fraction, over the height of the second segment, into two second fractions $TR_{4,1}$ and $TR_{4,2}$, in "block" form (or "paving stones"). If the maximum variation amplitude for the thigh perimeter is 12 cm, the blocks preferably exhibit a height of 12 cm, and are preferably contiguous to one another.

If only two parameters have been chosen in the step a), the "blocks", which constitute coverage zones, cover substantially all the population of the representative sample after the subdivision of each of the first fractions.

More specifically, the set of blocks must cover a percentage of the individuals of the sample greater than the desired coverage rate.

Each coverage zone T0, T1, T1+, T2, T2+, T3, T3+ and T4 covers a portion of the population that a particular orthesis will be able, by deformation, to satisfy.

The number of coverage zones is preferably minimized by maximizing the widths of the fractions according to the deformation capacity of the orthesis of the model. As an example, if a model comprises two sizes and the ankle perimeter can vary to an extent of 2 cm and 2.5 cm (possible variation amplitude for the ankle perimeter) for the two sizes, respectively, the maximal variation amplitude is 2 cm.

In a preferred embodiment, the "blocks" are arranged as follows:

If a single block is enough to cover substantially all of a first fraction, it is arranged so as to cover as many individuals as possible in this first fraction.

Otherwise, the median of the first fraction is sought, that is to say the value for the second parameter which separates the first fraction into two sub-populations comprising the same number of individuals. The paving is then begun by placing two blocks on either side of the median. The placement of the blocks is then continued substantially to the ends of the first segment of said first fraction. The set of blocks of said first fraction can then be moved to the highest or the lowest values of the second parameter, so as to cover as many individuals as possible in this first fraction and/or to try to eliminate one of the two blocks at the ends of the first fraction considered. In particular, it is possible, after the initial placement of the blocks from the median, for the blocks at the ends of the first fraction to comprise a reduced number of individuals and for the movement of the set of blocks of the first fraction to make it possible to eliminate one of these blocks without the coverage rate being substantially diminished.

If the number of parameters is greater than 2, the process described above is repeated with each of the other parameters.

For example, with a third morphological parameter, each block previously described would therefore correspond to a column, the height of which would be oriented on the axis of the third parameter. In the same way as each first fraction was divided into second fractions, each second fraction would be subdivided into third fractions. By graphic representation, each column corresponding to a second fraction would therefore be subdivided into parallelepipeds with a height that would preferably be equal to the maximum variation amplitude of the third parameter.

Each coverage zone therefore corresponds to an intersection of a fraction for the first parameter, of a fraction for the second parameter, etc., that is to say, more generally, of the intersection of different fractions for each of the different parameters.

Generally, preferably, regardless of n, the width of the $n^{th}$ fractions is equal to the maximum variation amplitude of the $n^{th}$ parameter. The number of $n^{th}$ fractions is advantageously minimal.

Preferably, regardless of n, the $n^{th}$ fractions are not superimposed, that is to say that no individual is included in two $n^{th}$ fractions. The method thus best exploits the deformation capacities of the model.

Preferably, the coverage zones do not intersect.

The set of coverage zones determines the size grid.

Advantageously, this grid exhibits a minimum of sizes while guaranteeing a maximized coverage of the population.

A method according to the invention was implemented for an orthesis model. Advantageously, the number of sizes was reduced from 14 to 8, which represents a considerable advance.

The method led to the following size grid, corresponding to the coverage zones of FIG. 2, the perimeters being in cm.

| AUTOFIX HOSE Thigh perimeter | | | | | | | | |
|---|---|---|---|---|---|---|---|---|
| AUTOFIX HOSE | T0 | T1 | T1+ | T2 | T2+ | T3 | T3+ | T4 |
| Ankle perimeter | 16-19 | | 19-22 | | 22-25 | | 25-28 | 28-31 |
| Thigh perimeter | 45-57 | 42-54 | 54-66 | 47-59 | 59-71 | 53-65 | 65-77 | 62-74 |

From measurements of the ankle and thigh perimeters of a patient, this grid indicates a suitable size.

This size grid corresponds to the following size points (in cm, rounded to 0.5 cm):

| AUTOFIX HOSE | T0 | T1 | T1+ | T2 | T2+ | T3 | T3+ | T4 |
|---|---|---|---|---|---|---|---|---|
| Ankle perimeter at rest | 14.5 | 15.5 | 15.5 | 17.5 | 17.5 | 19 | 19 | 20.5 |
| Thigh perimeter at rest | 28 | 28.5 | 32 | 30 | 33.5 | 33.5 | 36 | 35.5 |

Another application of the method led to the following size grid:

| HALF HOSE Ankle perimeter | | | | | | | | |
|---|---|---|---|---|---|---|---|---|
| HALF HOSE | T0 | T1 | T1+ | T2 | T2+ | T3 | T3+ | T4 |
| Calf perimeter | 28-36 | 26-34 | 34-42 | 30-38 | 38-46 | 34-42 | 42-50 | 40-48 |
| Ankle perimeter | 16-19 | | 19-22 | | 22-25 | | 25-28 | 28-31 |

This size grid corresponds to the following size points (in cm, rounded to 0.5):

| HALF HOSE | T0 | T1 | T1+ | T2 | T2+ | T3 | T3+ | T4 |
|---|---|---|---|---|---|---|---|---|
| Calf perimeter at rest | 20.5 | 19.5 | 21 | 22 | 23 | 24.5 | 25 | 26 |
| Ankle perimeter at rest | 14 | 15.5 | 15.5 | 17 | 17 | 18 | 19 | 20.5 |

In these examples, the perimeters of the ankle, calf and thigh were measured at the levels where the ankle is thinnest and where the calf and the thigh are widest, respectively.

From the sizes obtained, it is possible to manufacture ortheses but also corresponding templates.

Obviously, the invention is not limited to the embodiments described and represented, supplied purely for illustrative purposes.

The invention claimed is:

1. Method for determining a size grid for an elastic vein compression orthesis model, said method comprising the following steps:
    a) determination of N morphological parameters, N being greater than or equal to 2;
    b) acquisition of a set of values of said parameters for a sample of a targeted population of individuals, each individual of the sample being associated with an individual point supplying, for each parameter, a value of said parameter;
    c) independently of the steps a) and b), determination of a rate of coverage of said sample to be covered by said grid, or desired "coverage rate", the desired coverage rate determining the percentage of the individuals of the sample for which at least one size of the model will be able to be appropriate;
    d) determination of a set of coverage zones, each coverage zone being a set of individual points relating to a set of individuals for which a same orthesis according to said model is adapted and thus corresponding to a size adapted to said set of individuals;
the number of coverage zones being determined so that the percentage of individual points included in at least one coverage zone is greater than or equal to said desired coverage rate,
the set of sizes corresponding to said coverage zones defining said size grid, the step d) comprising the following steps:
    d1) for a first of said parameters $p_1$, subdivision into "first fractions" of a "first segment" representing all the values of the first parameter between the minimum and maximum bounds of the first parameter, said minimum and maximum bounds being determined such that said first segment covers more than 80% of the number of individuals of the sample;
    d2) successively, for each $n^{th}$ parameter $p_n$, from the second parameter to the last parameter $p_N$, for each $(n-1)^{th}$ fraction, subdivision into $n^{th}$ fractions of an $n^{th}$ segment representing all the values of the $n^{th}$ parameter lying between the minimum and maximum bounds, said minimum and maximum bounds being determined such that said $n^{th}$ segment covers more than 80% of the number of individuals of the $(n-1)^{th}$ fraction considered;
    said segments being subdivided so as to define, after the processing of the last parameter, a set of coverage zones together covering a percentage of the population of the sample greater than or equal to the desired coverage rate, each coverage zone consisting of a set of points each defined by N coordinates, all the $i^{th}$ coordinates of the points of a same coverage zone belonging to a same $i^{th}$ fraction, the width of an $n^{th}$ fraction being less than or equal to the maximum variation amplitude of the values of the $n^{th}$ parameter considering any orthesis according to said model, and greater than 0.8 times said amplitude.

2. Method according to claim 1, in which the width of an $n^{th}$ fraction is greater than 0.9 times said amplitude.

3. Method according to claim 1, in which one of the said parameters is the ankle perimeter and the maximum variation amplitude of the values of this parameter is comprised between 2 and 4 cm, the width of the fractions resulting from the subdivision of the segment related to the ankle perimeter being less than or equal to said amplitude and greater than 0.8 times said amplitude.

4. Method according to claim 1, in which one of the said parameters is the thigh perimeter and the maximum variation amplitude of the values of this parameter is comprised between 8 and 14 cm, the width of the fractions resulting from the subdivision of the segment related to the thigh perimeter being less than or equal to said amplitude and greater than 0.8 times said amplitude.

5. Method according to claim 1, in which, in the step a), the parameters are chosen from the group consisting of a calf dimension, a thigh dimension, and an ankle dimension.

6. Method according to claim 1, in which, in the step b), the targeted population is a part of the population more likely to be affected by the treatment by the orthesis model than the rest of the population.

7. Orthesis having a size from a size grid determined according to a method according to claim 1.

8. Orthesis according to claim 7, having, at rest, dimensions within the following ranges $P_i$, in cm:

| Ranges | | P0 | P1 | P2 | P3 | P4 | P5 | P6 | P7 |
|---|---|---|---|---|---|---|---|---|---|
| Ankle perimeter at rest | min | 14 | 15 | 15 | 17 | 17 | 18.5 | 18.5 | 20 |
| | max | 15 | 16 | 16 | 18 | 18 | 19.5 | 19.5 | 21 |
| Thigh perimeter at rest | min | 27.5 | 28 | 31.5 | 29.5 | 33 | 33 | 35.5 | 35 |
| | max | 28.5 | 29 | 32.5 | 30.5 | 34 | 34 | 36.5 | 36 | or within the following ranges $P_i'$, in cm:

| Ranges | | P0' | P1' | P2' | P3' | P4' | P5' | P6' | P7' |
|---|---|---|---|---|---|---|---|---|---|
| Calf perimeter at rest | min | 20 | 19 | 20.5 | 21.5 | 22.5 | 24 | 24.5 | 25.5 |
| | max | 21 | 20 | 21.5 | 22.5 | 23.5 | 25 | 25.5 | 26.5 |
| Ankle perimeter at rest | min | 13.5 | 15 | 15 | 16.5 | 16.5 | 17.5 | 18.5 | 20 |
| | max | 14.5 | 16 | 16 | 17.5 | 17.5 | 18.5 | 19.5 | 21 |

9. Set of ortheses of different sizes, according to a same model, each of said ortheses having, at rest, dimensions within one of the following ranges $P_i$

| Ranges | | P0 | P1 | P2 | P3 | P4 | P5 | P6 | P7 |
|---|---|---|---|---|---|---|---|---|---|
| Ankle perimeter at rest | min | 14 | 15 | 15 | 17 | 17 | 18.5 | 18.5 | 20 |
| | max | 15 | 16 | 16 | 18 | 18 | 19.5 | 19.5 | 21 |
| Thigh perimeter at rest | min | 27.5 | 28 | 31.5 | 29.5 | 33 | 33 | 35.5 | 35 |
| | max | 28.5 | 29 | 32.5 | 30.5 | 34 | 34 | 36.5 | 36 | or each of said ortheses having, at rest, dimensions within one of the following ranges $P_i'$:

| Ranges | | P0' | P1' | P2' | P3' | P4' | P5' | P6' | P7' |
|---|---|---|---|---|---|---|---|---|---|
| Calf perimeter at rest | min | 20 | 19 | 20.5 | 21.5 | 22.5 | 24 | 24.5 | 25.5 |
| | max | 21 | 20 | 21.5 | 22.5 | 23.5 | 25 | 25.5 | 26.5 |
| Ankle perimeter at rest | min | 13.5 | 15 | 15 | 16.5 | 16.5 | 17.5 | 18.5 | 20 |
| | max | 14.5 | 16 | 16 | 17.5 | 17.5 | 18.5 | 19.5 | 21 |

10. Size grid of an orthesis model determined according to a method according to claim 1.

11. Template of a lower limb of an animal body, in particular human, the dimensions of which correspond to a size from a size grid determined according to a method according to claim 1.

12. Kit comprising
a database containing, for at least two morphological parameters, parameter values for a sample of individuals representative of a targeted population, and
a template corresponding to a size from a size grid determined according to a method according to claim 1.

\* \* \* \* \*